United States Patent [19]

Weeks

[11] Plant 4,695

[45] Apr. 21, 1981

[54] ROSE PLANT

[76] Inventor: O. L. Weeks, 4759 Philadelphia St., Chino, Calif. 91710

[21] Appl. No.: 121,917

[22] Filed: Feb. 15, 1980

[51] Int. Cl.[3] ..... A01H 5/00

[52] U.S. Cl. ..... Plt./20

[58] Field of Search ..... Plt./20

*Primary Examiner*—Robert E. Bagwill
*Attorney, Agent, or Firm*—Vincent G. Gioia

[57] ABSTRACT

A new floriferous hybrid tea rose variety of attractive red coloring, retaining eye appeal upon aging.

1 Drawing Figure

The present invention relates to a new and distinct variety of rose plant of the hybrid tea rose class, which was originated by my crossing as seed parent an unpatented, unreleased and unnamed seedling of my creation and the rose known as "First Prize" as pollen parent.

Among the novel characteristics possessed by this new variety which distinguish it from its parents and all other varieties of which I am aware are its attractive red coloring which does not blue upon aging and which retains its vibrant color in hot weather. The vigorous, free-branching plant is very floriferous and strong stems support the good sized, heavily petaled flowers upright and erect. Asexual reproduction by budding of the new variety as performed in San Bernardino County, Calif., shows that the foregoing and other distinguishing characteristics come true to form and are established and transmitted through succeeding propagations.

My new variety has superior growth habit than its seed parent and different flower color than its pollen parent, "First Prize". A particularly outstanding feature of this new variety is its ability to remain attractive during hot weather.

The accompanying drawing shows typical specimens of the vegatative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "27A" is plate 27A of the Royal Horticultural Society Color Chart.

Parentage: Seedling.
*Seed parent.*—My unnamed seedling.
*Pollen parent.*—"First Prize".
Class: Hybrid tea.

The following observations are made of specimens grown outdoors in San Bernardino County, Calif. during the month of October.

1. FLOWER

Blooming habit: Intermittent to continuous.

A. *Bud.*—(1) Size: Small, short. (2) Form: Ovoid with some foliaceous appendages on green bud surface. (3) Color: When sepals first divide—46A to 46B with 27A at point of petal attachment. When petals begin to unfurl—46A to 46B. (4) Sepals: Ordinary shape, a little longer than bud, somewhat foliated. (5) Peduncle: Length—Medium. Aspect—Straight. Strength—Erect, strong. Color—139B.

B. *Bloom.*—(1) Size: Average size when fully expanded—about 4 to 4½ inches. (2) Borne: Singly and in small clusters of two to three blooms. (3) Form: Cupped or ovoid at first becoming flat upon opening, petals roll out and down as flower opens. (4) Petalage: Number of petals under normal conditions—about 48 to 54, and opens well. (5) Color: Color begins as currant red bud upon first petals unfurling and lightens to 44C and 44D at ⅓ to ½ open. Also at this stage ruffling of petal edges is evident. Veining of petals becomes increasingly noticeable as flower ages. Fully open older blooms are a combination 44C and 44D with the veins appearing somewhat darker and additionally with highlights of 46B. Random lightening as in sun bleaching is noticeable on fully opened older blooms. The pale yellowish/-cream coloring at petal point of attachment (seen in tight buds after sepals divide) is not readily visible as the flower opens and matures.

C. *Petals.*—(1) Texture: Thick. (2) Appearance: Satiny. (3) Form: Scalloped with apex flat, ruffled. (4) Arrangement: Regularly arranged. (5) Petaloids in center: Few. (6) Persistence: Drop off cleanly. (7) Fragrance: Moderate. (8) Lasting quality: Long lasting on plant and as cut flower.

2. REPRODUCTIVE ORGANS

A. Stamens, filaments and anthers:
(1) *Arrangement.*—Regular.
B. Pollen: Color—gold yellow.
C. Styles: Uneven, medium length, bunched.
D. Stigmas: Yellow.
E. Hips: None observed.

3. PLANT

A. Form: Upright, tall, bushy.
B. Growth: Vigorous, free branching.
C. Foliage: Compound 3, 5 and 7 leaflets, new growth is reddish bronze to green with light green veining.
(1) *Size.*—Medium.
(2) *Quantity.*—Abundant.
(3) *Color.*—New foliage: very new growth begins reddish and becomes green upon maturing. Upper side—near to 136B. Old foliage: Upper side—near to 136A.
(4) *Shape.*—Ovoid, mucronate.

(5) *Texture.*—Thick, leathery, wrinkled.
(6) *Edge.*—Coarsely serrated.
(7) *Serration.*—Simple.
(8) *Leaf stem.*—Color—near to 139B.
(9) *Stipules.*—Medium, wide.

D. Wood:
(1) *New wood.*—Color—near 139B. Bark—smooth, shiny.
(2) *Old wood.*—Color—near 139A. Bark—smooth, shiny.

E. Thorns:
(1) *Thorns.*—Quantity (main stalk): ordinary Form—recurved. Length—ordinary. Color—on new wood 139B, tan on older wood. Position—scattered.
(2) *Prickles.*—Few.

I claim:

1. A new and distinct variety of rose plant of the hybrid tea class, substantially as shown and described, characterized particularly by a floriferous, vigorous, free branching plant producing heavily petalled flowers of red coloring borne singly to a stem and in small clusters and which retain their attractiveness upon aging as well as in hot weather.

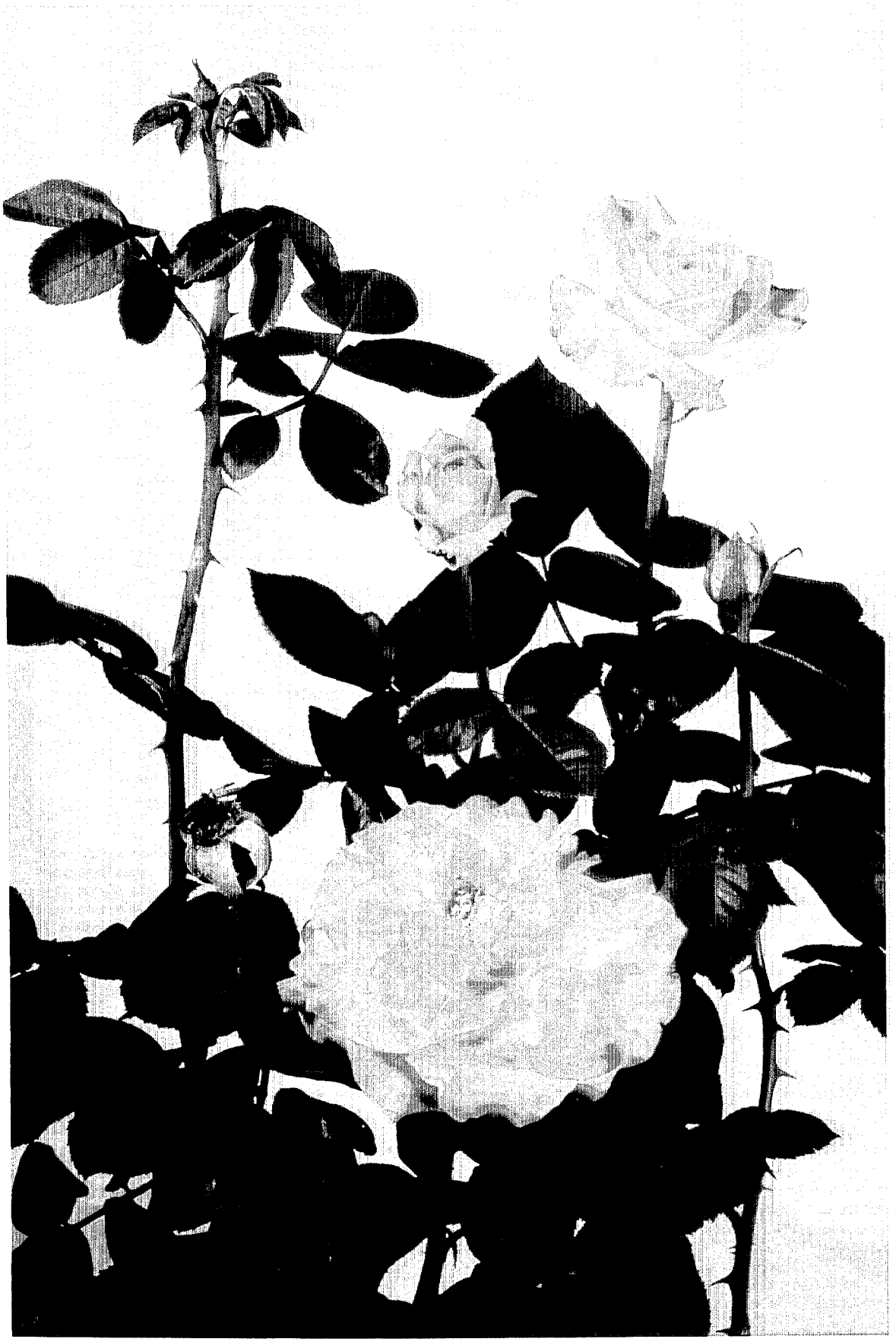

* * * * *